United States Patent [19]

Snyder et al.

[11] Patent Number: 4,725,588

[45] Date of Patent: Feb. 16, 1988

[54] ALKYL PHOSPHOLIPID ANTIHYPERTENSIVE AGENTS IN METHOD OF LOWERING BLOOD PRESSURE

[75] Inventors: Fred L. Snyder; Merle L. Blank, both of Oak Ridge; Ernest E. Muirhead, Memphis; Byron E. Leach, deceased, late of Memphis, by Ellanor L. L. Leach, executor; Lawrence W. Byers, Memphis, all of Tenn.

[73] Assignee: The United States of America as represented by the United States Department of Energy, Washington, D.C.

[21] Appl. No.: 232,790

[22] Filed: Feb. 9, 1981

Related U.S. Application Data

[63] Continuation of Ser. No. 92,156, Nov. 7, 1979, abandoned.

[51] Int. Cl.$^4$ .............................................. A61K 31/66
[52] U.S. Cl. ...................................... 514/114; 514/76; 514/77; 558/169
[58] Field of Search ...................... 260/925, 944, 945; 424/199, 211; 514/76, 77, 114; 558/169

[56] References Cited

U.S. PATENT DOCUMENTS 4,329,302  5/1982  Hanahan et al. .................... 260/925

Primary Examiner—Richard L. Raymond
Attorney, Agent, or Firm—Irving Barrack; Stephen D. Hamel; Judson R. Hightower

[57] ABSTRACT

The composition of this invention is 1-O-alkyl-2-acetoyl-sn-glycero-3-phosphocholine, having the ionic structural formula;

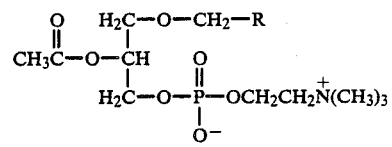

wherein R is saturated alkyl having 9-21 carbon atoms, or salts or hydrates of the composition. Preferably R has 13-19 carbon atoms and most preferably R has 15 carbon atoms. The composition of this invention is useful for reducing hypertension in warm-blooded animals, including humans, when administered either orally or by injection or innoculation, e.g., intravenous injection. The composition can be prepared from naturally occurring lipids or synthetically from commercially available material.

2 Claims, 4 Drawing Figures

ALKYL PHOSPHOLIPID ANTIHYPERTENSIVE AGENTS IN METHOD OF LOWERING BLOOD PRESSURE

This is a continuation of application Ser. No. 92,156, filed Nov. 7, 1979, now abandoned.

BACKGROUND OF THE INVENTION

1. Field of the Invention

The invention relates to the control of hypertension (high blood pressure) in human or veterinary medicine by the administration of pharmaceutical agents having hypotensive activity. It is a result of a contract with the U.S. Department of Energy.

2. Description of the Prior Art

In describing the work of others herein we do not admit that such work is actually prior art under 35 USC 102 or 35 USC 103 or that the work was actually prior in time to the making of the invention described and claimed herein. We reserve the right to establish a date of conception or reduction to practice prior to the effective date of any publication, patent, or work herein described.

Muirhead et al in "Reversal of Hypertension by Transplants and Lipid Extracts of Cultured Renomedullary Interstitial Cells," Laboratory Investigation Vol. 35, No. 2, pp. 162-172 (1977) describe the antihypertensive activity of lipids of unidentified chemical structure extracted from renal medulla tissue. The extracted material was subjected to reduction with $NaAlH_2(OCH_2CH_2OCH_3)_2$, acetic acid treatment and lipophilic chromatography on Sephadex (registered trademark). In some instances the material was subjected to chromatography on Florisil (registered trademark) and acetylation with acetic anhydride prior to Sephadex chromatography. The treated material demonstrated hypotensive activity in rats and rabbits. The active agents in the material were not identified or separated from other components. A compound isolated from bovine brain, which in some respects resembled lysophosphatidylcholine was shown to depress blood pressure in Tsukatani et al, Chemical Pharmaceutical Bulletin (Tokyo) Vol. 24 p p. 2294-1200 (1976).

STATEMENT OF THE OBJECTS

It is an object of this invention to provide a highly effective antihypertensive composition for use in human and veterinary medicine.

It is a further object to provide a method for preparing the antihypertensive agent from readily available commercial materials.

It is a further object to provide a method for reducing blood pressure in warm-blooded animals, including humans.

Other objects, advantages, and novel features of the invention will become apparent to those skilled in the art upon examination of the following detailed description and accompanying drawings.

SUMMARY OF THE INVENTION

The composition of this invention is 1-O-alkyl-2-acetoyl-sn-glycero-3-phosphocholine, having the ionic structural formula:

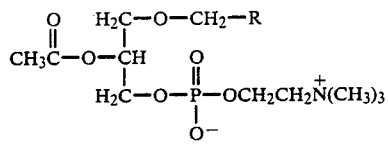

wherein R is saturated alkyl having 9-21 carbon atoms, or salts or hydrates of the composition. Preferably R has 13-19 carbon atoms and most preferably R has 15 carbon atoms. The composition of this invention is useful for reducing hypertension in warm-blooded animals, including humans, when administered either orally or by innoculation, e.g., intravenous injection.

DETAILED DESCRIPTION OF THE INVENTION

Figure 1:
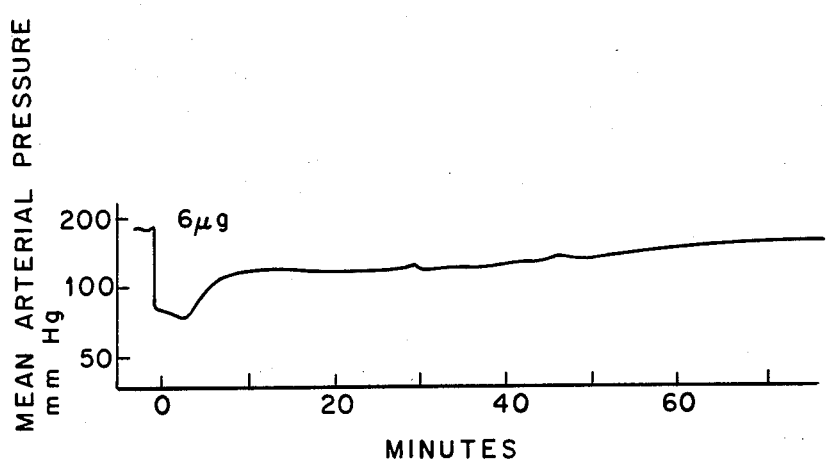
FIG. 1 is a data tracing illustrating the mean arterial pressure response of a hypertensive rat to intravenous injection of the agent of this invention.

This invention is based upon the discovery that phospholipids having the structure in ionic form:

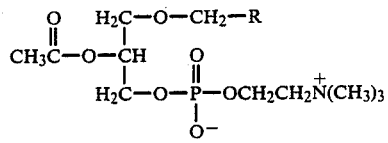

demonstrate profound hypotensive activity in warm-blooded animals. The R substituent of the phospholipid of this invention is straight chain or branched saturated alkyl having 9-21 carbon atoms. The above phospholipid is designated 1-O-alkyl-2-acetoyl-sn-glycero-3-phosphocholine, in accordance with stereospecific numbering as described in "The Nomenclature of Lipids," IUPAC-IUB Commission on Biochemical Nomenclature, Lipids, Vol. 12, No. 6, pp. 455-468 (1977). 1-O-alkyl-2-acetoyl-sn-glycero-3-phosphocholines exist as amorphous gummy solids at room temperature and are generally light yellow in color. The 1-O-alkyl-2-acetoyl-sn-glycero-3-phosphocholine compositions can also exist as a salt or as a hydrate. In the salt form, a cation would be associated with the negatively charged site of the structure and an anion would be associated with the positively charged site. As a hydrate, a hydrogen atom would be associated with the negative site and a hydroxyl group with the positive site. The composition, its salt and its hydrates are soluble in aqueous and organic solutions. The compositions can be readily synthesized in a highly pure form from lipids occurring in nature, and from commercially available materials.

For pharmaceutical applications the phospholipid should be administered as a composition of matter consisting essentially of the 1-O-alkyl-2-acetoyl-sn-glycero-3-phosphocholines, and which can include pharmaceutical carriers. By "consisting essentially of" it is meant free from impurities or other components in amounts sufficient to materially degrade the antihypertensive activity of the phospholipid. The antihypertensive agent of this invention consists essentially of material having the ionic structural formula:

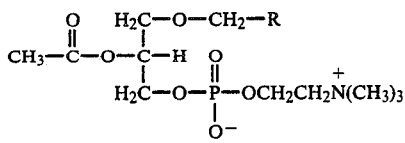

wherein R is saturated alkyl having 9–21 carbon atoms, or salts or hydrates thereof, in combination with a pharmacologically compatible carrier. Pharmacologically compatible carriers are liquid or solid substances which do not interfere with the anti-hypertensive activity of the phospholipid. Examples of such carriers for intravenous or oral administration are water, saline or other aqueous solution, emulsions, ethanol solutions, albumin solutions, emulsions with propylene glycol or glycerine and liposomal preparations. For oral administration the phospholipids can be administered in solid form in capsules or in tablets. Conventional solid pharmaceutical carriers such as starch-lactose mixtures and Avicel (registered trademark), a microcrystalline cellulose, can be used if desired. The phospholipids of this invention can be administered singly or as a mixture of alkyl homologues, where R in the 1-O-CH$_2$-R group can vary from 9–21, preferably 13–19 carbon atoms.

It is important that the composition be substantially free from toxic imputities which can cause undesirable side effects. Phosphocholine lipids having a lyso group (—OH) at position 2 are known to cause hemolysis. Consequently, the composition of matter of this invention consisting essentially of 1-O-alkyl-2-acetoyl-sn-glycero-3-phosphocholine should be substantially free of 2-lyso-sn-glycero-3-phosphocholines such as 1-O-alkyl-2-lyso-sn-glycero-3-phosphocholines having the ionic structural formula:

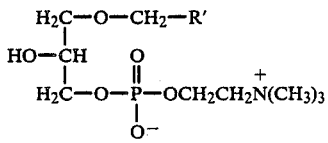

wherein R' is an aliphatic hydrocarbon group, or salts or hydrates thereof.

In its method of use aspects this invention comprises depressing blood pressure in a warm-blooded animal, including human beings, by administering to the animal an amount of the 1-O-alkyl-2-acetoyl-sn-glycero-3-phosphocholines effective to reduce the blood pressure of the animal. Based on tests with hypertensive rats the effective dosage of 1-O-alkyl-2-acetoyl-sn-glycero-3-phosphocholine to provide an antihypertensive effect lasting up to about 48 hours is about 0.025–0.060 milligram per kilogram body weight for intravenous administration and about 0.040–0.20 milligram per kilogram body weight for oral administration. Effects of shorter duration can be achieved with smaller dosages.

1-O-alkyl-2-acyl-sn-glycero-3-phosphocholines having 18-carbon acyl groups at the sn-2 position have shown to be ineffective for reducing blood pressure, however compositions having shorter sn-2 acyl groups, such as 3–5 carbon atoms can be expected to exhibit hypotensive activity. Such 1-O-alkyl-2-acyl-sn-glycero-3-phosphocholines demonstrating hypotensive activity are contemplated as equivalents to 1-O-alkyl-2-acetoyl-sn-glycero-3-phosphocholines in the compositions and methods of this invention.

The phospholipids of this invention can be prepared from naturally occurring lipids such as occur in heart tissue or they can be prepared from commercially available sources. In one synthesis method, a lipid composition of the ionic formula

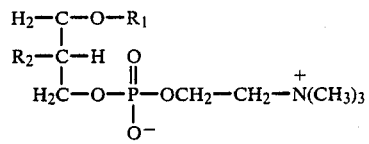

wherein $R_1$, is a saturated or unsaturated aliphatic hydrocarbon radical having 10–22 carbon atoms, preferably 14–20, and most preferably 16 carbon atoms, and $R_2$ is an acyl group, is saponified by reaction with a base such as sodium or potassium hydroxide to form the 2-lyso phospholipid:

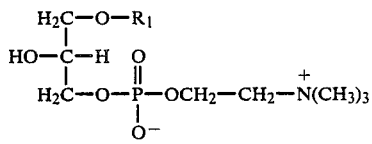

The 2-lyso-phospholipid can be hydrogenated to saturate the $R_1$ group if necessary. The hydrogenation step can alternatively be carried out before saponification. The 1-O-alkyl-2-lyso-sn-glycero-3-phosphocholine is then acetylated by reacting with an acetylating agent, such as acetic acid, acetyl chloride, or acetic anhydride to produce 1-O-alkyl-2-acetoyl-sn-glycero-3-phosphocholine, which is recovered from the reaction mixture, e.g., by thin layer chromatography.

The antihypertensive agent can also be prepared from a racemic mixture of O-alkyl-phospholipid stereoisomers by reacting a first mixture containing 1-O-alkyl-2-acyl-sn-glycero-3-phosphocholine and 3-O-alkyl-2-acyl-sn-glycero-1-phosphocholine with a lipase such as phospholipase A$_2$ which is specific for deacylating the sn-2 position of the natural (1-O-alkyl) isomer to provide a second mixture containing 1-O-alkyl-2-lyso-sn-glycero-3-phosphocholine. The 1-O-alkyl-2-lyso-sn-glycero-3-phosphocholine is then reacted with an acetylating agent, such as acetic anhydride, acetic acid, or acetyl chloride to produce 1-O-alkyl-2-acetoyl-sn-glycero-3-phosphocholine, which is separated, e.g., by thin layer chromatography, from unreacted material.

The antihypertensive agent of this invention can be prepared from a 1-O-alkyl glycerol by reacting the alkyl glycerol with a benzyl halide such as benzyl chloride to produce a 1-O-alkyl-2-lyso-3-benzyl composition having the structural formula

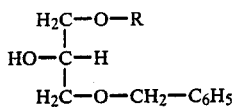

This product is reacted with an acetylating agent such as acetic anhydride, acetyl chloride, or acetic acid to acetylate the sn-2 position, producing a product having the formula

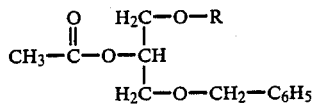

This product is reacted with hydrogen, in the presence of a hydrogenation catalyst if desired, to produce 1-O-alkyl-2-acetoyl-sn-glycerol which is reacted with a phosphating agent such as POCl₃ to produce a reaction product having the structural formula

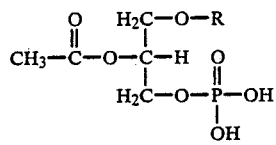

This product is reacted with choline-p-toluene sulfonate, $CH_3-CH_4H_4-SO_3-CH_2CH_2N^+(CH_3)_3$, to produce 1-O-alkyl-2-acetoyl-sn-glycero-3-phosphocholine which can be recovered from the reaction mixture using the chromatographic methods described.

The following examples illustrate the laboratory scale preparation and testing of phospholipids according to this invention. The synthetic methods can readily be amplified to large scale, for example, by using high pressure liquid chromatography procedures.

EXAMPLE I

Preparation of 1-O-alkyl-2-acetoyl-sn-glycero-3-phosphocholine from Heart Tissue (a) Extraction of Lipids One hundred grams of fresh beef heart (obtained from a slaughterhouse) was minced, 500 ml of chloroform was added, and the mixture was homogenized in a Polytron blender. Methanol (500 ml) was added and the mixture again homogenized in the blender. The homogenate was centrifuged at 1850 rpm for 10 minutes in a refrigerated centrifuge to pellet proteins. To the solvent extract (750 ml) was added 390 ml water with vigorous stirring. This mixture was transferred into 40 ml centrifuge tubes and centrifuged at 1850 rpm for 10 minutes, whereupon the solution separated into a water-methanol phase and a chloroform phase which contained most of the dissolved lipids. The chloroform phases were pooled and transferred to a rotary evaporator to remove the solvent. The lipid residue was dissolved in chloroform for chromatographic analysis.

(b) Isolation of 1,2-diradyl-sn-glycero-3-phosphocholine

The lipid residue contained a mixture of compounds of the formula:

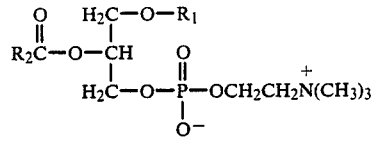

where $R_1$ is generally a mixture of alk-1-enyl, alkyl, and acyl groups and $R_2$ is an aliphatic group. Approximately 50 mole percent of the lipid fraction was 1-alk-1-enyl-2-acyl-sn-glycero-3-phosphocholine. The lipid fraction was separated by thin layer chromatography by banding the lipid solution onto an 8"×8" glass TLC plate coated with silica gel HR (MC/B Manufacturing Chemists, Inc., Cincinnati, Ohio) and employing a developing solvent of chloroform:methanol:glacial acetic acid:water (50:25:8:4 respectively by volume). A phosphatidylcholine-containing standard (isolated from rat liver) was used. Similar chromatographic results can be obtained using egg phosphatidylcholine. The phospholipid fraction had an $R_f$ (migration distance relative to the solvent front) about the same as the phosphatidylcholine standard. With a developing solvent of chloroform:methanol:glacial acetic acid:water (50:25:8:3) the phospholipid fraction has an average $R_f$ of 0.25, ranging from 0.22–0.28, on the silica gel. As is customary in the art, iodine staining was used to identify the segregated lipids in one track of the TLC plate. The portion of the silica gel plate containing the unstained phospholipid fraction was scraped away. The phospholipids were eluted from the loaded silica gel by washing with a solution prepared from 3.5 ml H₂O, 6.5 ml methanol containing 2% acetic acid, and 7 ml chloroform. The eluate formed two phases, the lipids distributing to the chloroform phase.

(c) Hydrogenation of Carbon-Carbon Double Bonds

The isolated phospholipid fraction from step (b) was dried with N₂ and 3 ml ethanol, containing about 25 mg Adam's catalyst (PtO₂.H₂O), was added. Hydrogen was gently sparged through the mixture for about 20 seconds and the sample was capped and shaken. The hydrogen sparging was repeated twice more. Chloroform (3 ml) was added and the mixture was centifuged to separate the catalyst. The supernatant was removed, the catalyst was rinsed with 2:1 chloroform:methanol, and the supernatants were combined. The supernatants were dried with N₂ and the residue was dissolved in 6 ml of 2:1 chloroform-methanol. After hydrogenation, a portion of the product was tested by exposure to HCL. No released aldehydes were detected, indicating that no plasmalogens (alk-1-enyl groups) existed in the hydrogenated lipid.

(d) Replacement of Acyl Group at Position 2 with An Acetoyl Group

After hydrogenation, the product was mildly saponified to remove acyl groups by adding 0.6 ml of 0.33N potassium hydroxide in methanol to the sample dissolved in 1.2 ml of chloroform, followed by mild shaking for 20 minutes at room temperature. The saponification mixture was cooled at 0° C., and 0.5 ml of 6N HCl, 0.8 ml chloroform, 1.2 ml of methanol, and 1.5 ml of water were added to neutralize the potassium hydroxide. The mixture of solvents formed two phases, with the chloroform phase containing the deacylated lipid product. After centrifugation at 1500 rpm for 10 minutes the lower chloroform layer was removed and the upper layer was extracted twice more with chloroform. The three chloroform extracts were combined and evaporated to dryness. The products, which are 2-lyso-phospholipids, were separated from fatty acids by preparative thin layer chromatography using the same type of silica gel plates and developing solvent as in step (b) with the phosphatidylcholine (from rat liver) standard. The lyso-phospholipid product has about the same $R_f$ as lyso-phosphatidylcholine and was recovered from the plate and eluted from the silica gel as in step (b). With a developing solvent of chloroform:methanol:glacial acetic acid:water (50:25:8:3) the lyso-phospholipid product has a rather sharp $R_f$ of 0.11 on the silica gel. The lyso-phospholipid is 1-O-alkyl-2-lyso-sn-glycero-3-phosphocholine having the formula:

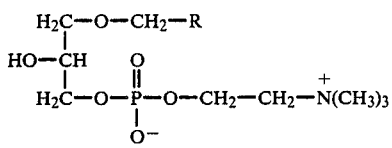

The lyso-phospholipid was acetylated by heating the samples in 2.5 ml of acetic anhydride:pyridine (4:1, vol./vol.) for 45 minutes at 65°-70° C. Heating at 100° C. for one hour is now preferred. Excess acetic anhydride and pyridine were removed at a temperature of 60°-70° C. with a stream of $N_2$. The acetylated compounds were isolated from lyso-compounds by preparative thin layer chromatography using the same type of silica gel plates and developing solvent as described in step (b). The standard was the rat liver phosphatidylcholine. The 1-O-alkyl-2-acetoyl-sn-glycero-3-phosphocholine product had a slightly lower $R_f$ than the phosphatidylcholine standard and the 2-lyso-phospholipid had an $R_f$ lower than the 2-acetoyl product. The 1-O-alkyl-2-acetoyl-sn-glycero-3-phosphocholine product was extracted from the silica gel as described in step (b), and, after evaporation of solvents, is ready for use. With a developing solvent of chloroform:methanol:glacial acetic acid:water (50:25:8:3) the 1-O-alkyl-2-acetoyl-sn-glycero-3-phosphocholine has an $R_f$ of about 0.11±0.01. The nuclear magnetic resonance spectrum for this composition showed positions of the proton signals for the acetoyl and the three N-terminal methyl groups which agree with the spectra described for triacetin and phosphatidylcholine by Chapman et al., J. Biol. Chem. 241, pp. 5044-5052 (1966). It has been determined that better recovery is obtained when the saponification is performed before the hydrogenation step due to the solubility of the lyso-compound in the hydrogenation solvent. Acetic acid (10%), rather than HCl, should then be used for the neutralization step.

The length of the alkyl chain in the 1-O-alkyl-2-acetoyl-sn-glycero-3-phosphocholine was determined by reduction of the composition with $NaAlH_2(OCH_2OCH_3)_2$ to form alkylglycerols which were treated with 1 ml acetone containing 0.5 μl of 70% $HClO_4$ acid for 5 minutes at room temperature to prepare isopropylidine derivatives. Analysis of the isopropylidenes by gas liquid chromatography showed the alkyl chain lengths, which correspond to R+1 in the structural formula of the 1-O-alkyl-2-acetoyl-sn-glycero-3-phosphocholine, as set forth in the table.

TABLE

| Carbons | Double Bonds | Branching | Weight Percent |
|---|---|---|---|
| 14 | 0 | yes | 1.6 |
| 14 | 0 | no | 1.3 |
| 15 | 0 | yes | 9.4 |
| 15 | 0 | no | 3.9 |
| 16 | 0 | yes | 2.4 |
| 16 | 0 | no | 65.7 |
| 17 | 0 | yes | 1.4 |
| 18 | 0 | no | 8.8 |
| 19 | 0 | no | 1.2 |
| 20 | 0 | yes | |

EXAMPLE II

Antihypertensive Activity Tests

The 1-O-alkyl-2-acetoyl-sn-glycero-3-phosphocholine of Example I was tested for antihypertensive activity at Baptist Memorial Hospital, Memphis, Tenn., under the direction of Drs. E. Eric Muirhead and Lawrence W. Byers by administration to members of a strain of hypertensive rats having one kidney. The rats had a clip reducing the flow of blood through the renal artery of the kidney. Each rat had a mean arterial pressure of 170-190 mm Hg. prior to administration, as obtained by averaging arterial pressure for the preceeding three days. The compound was administered in saline solution and in a saline solution containing albumin, both intravenously and by mouth. For the intravenous injection, a catheter was implanted in the inferior vena cava. For administration by mouth, the composition was passed through a tube directly into the stomach. Of the rats receiving the composition by mouth, one rat had a single dose of 13 micrograms and two rats each received a single dose of 20 micrograms. Seven rats received multiple doses of 40-80 micrograms each. Of the rats receiving the composition intravenously, single doses of 1.0-6.4 micrograms were given, or multiple doses, each amounting to 4-6 micrograms, were given for a total dose of 12-24 micrograms.

The acute effect of the intravenous doses was evaluated by a bolus injection while the arterial pressure was continuously recorded. The prolonged depressor effect was evaluated by introducing the compound, either intravenously or by mouth, at a slow rate with the arterial pressure not being allowed to decrease below 90-100 mm Hg. Two sets of controls were employed. A group of seven hypertensive rats were injected with the vehicle (0.4-0.5 ml of 0.9% saline). Another group of 16 hypertensive animals were injected with the acyl analogue of the alkyl ether lipid (an acyl group replacing the alkyl ether linkage at position 1), which showed no antihypertensive activity. Similar tests were run showing that a non-acetylated 1-O-alkyl phospholipid (—OH at position 2) was inactive as a blood pressure depressor agent.

FIG. 1 illustrates the acute depressor effect elicited by a single bolus intravenous dose of 6 micrograms of the composition of Example I. Within about 2 seconds, the arterial pressure receded from 185 to 50-70 mm. Hg, remaining maximally depressed for about 5 minutes, thereafter gradually increasing, but remaining 25 mm Hg below the original level after one hour.

Figure 2:
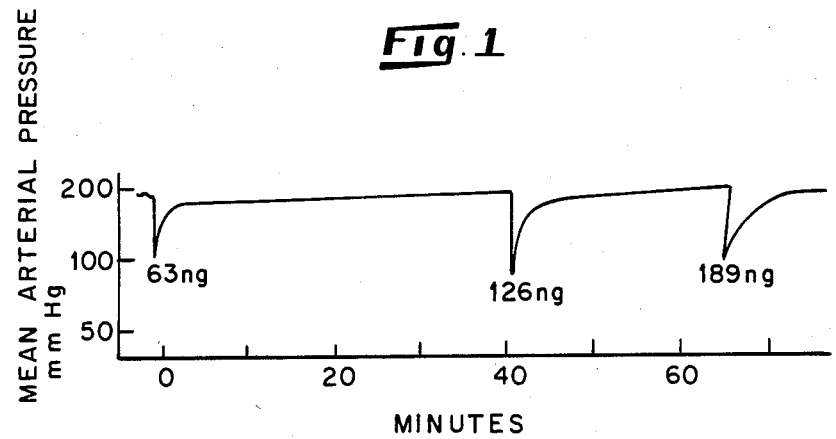
FIG. 2 is a data tracing illustrating the dose responses of mean arterial pressure of a hypertensive rat to the agent of this invention.

FIG. 2 illustrates the dose response of the acute depressor effect of the composition of Example 1 when 63, 126, and 189 nanograms were injected as a bolus. The immediate depressor effect amounted to −60, −85, and −95 mm Hg, respectively.

Figure 3:
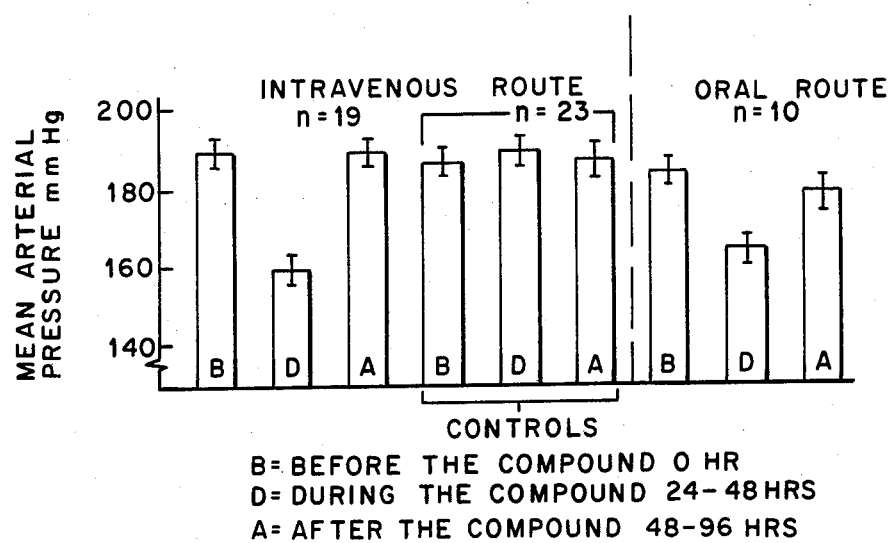
FIG. 3 is a histogram illustrating the duration of mean arterial pressure reduction in hypertensive rats from the intravenous and oral administration of the agent of this invention.

FIG. 3 summarizes the prolonged depressor effect of the composition of Example I when administered intravenously and by mouth by multiple doses totaling about 20-80 micrograms orally or 12-24 micrograms intravenously.

Figure 4:
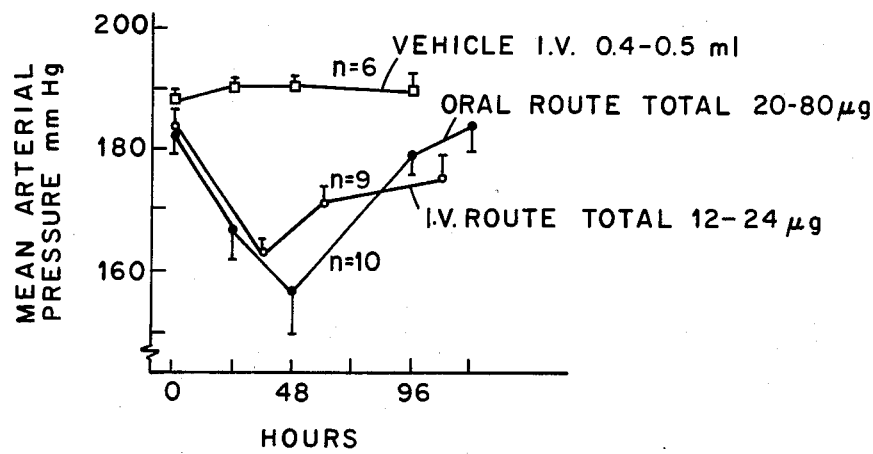
FIG. 4 is a graph showing the prolonged effect of mean arterial pressure reduction for hypertensive rats from the intravenous and oral administration of the agent of this invention.

FIG. 4 demonstrates change in mean arterial pressure over time for the animals receiving multiple doses of the composition of Example I. The controls had no change in mean arterial pressure.

EXAMPLE III

Preparation of 1-O-alkyl-2-acetoyl-sn-glycero-3-phosphocholine from 1-O-alkyl-2-acyl-phospholipids A racemic mixture (a powder) of the stereoisomers 1-O-hexadecyl-2-octadecenoyl-sn-glycero-3-phosphocholine and 3-O-hexadecyl-2-octadecenoyl-sn-glycero-1-phosphocholine, was obtained from R. Berchtold, Biochemisches Labor., Bern, Switzerland. The racemic mixture (7-10 mg) was dissolved in 3 ml of diethyl ether, to which was added 0.4 ml borate buffer (0.1M, pH 7.0) containing $CaCl_2$ ($2.5 \times 10^{-3}$M). To this mixture was added 4 mg of phospholipase $A_2$, obtained from *Ophiophagus hannah* venom (Ross Allan Reptile Institute, Silver Springs, Fla.). The mixture was shaken in a vortex mixer for two hours, then evaporated to dryness using $N_2$. The residue was extracted three times with chloroform-methanol (2:1) using 3.3 ml each time. The phospholipase $A_2$ is specific for the natural isomer (1-O-alkyl-), and converts it to the 2-lyso-composition. The extracts were pooled, evaporated to dryness, and the 2-lyso-composition was isolated by TLC as described in Example I. Two ml acetic anhydride and 0.5 ml pyridine were added to the isolated 2-lyso composition and the solutions heated to 100° C. for 1 hour to acetylate the 2-position of the natural isomer. The sample was blown to dryness with $N_2$ and redissolved in chloroform-methanol (2:1). The solution was banded on 4″ of an 8″ by 8″ plate coated with silica gel HR. The resulting 1-O-hexadecyl-2-acetoyl-sn-glycero-3-phosphocholine was separated by thin layer chromatography using the developing solvent and standard phosphatidylcholine of Example I. The 1-O-hexadecyl-2-acetoyl-sn-glycero-3-phosphocholine had an $R_f$ slightly lower than the standard phosphatidylcholine. The unreacted 3-O-hexadecyl-2-octadecenoyl-sn-glycero-1-phosphocholine and fatty acids had $R_f$ values the same as and higher, respectively, than the standard. The 1-O-hexadecyl-2-acetoyl-sn-glycero-3-phosphocholine had the formula

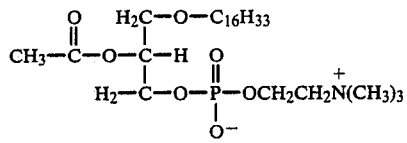

with no branching in the —$C_{16}H_{33}$ chain. Tests for hypotensive activity were performed on hypertensive rats as in Example II, and the composition showed essentially the same antihypertensive activity. The stereoisomer 3-O-hexadecyl-2-acetoyl-sn-glycero-1-phosphocholine was also prepared. The isomer showed only slight hypotensive activity which possibly was due to the presence of small amounts of the 1-O-alkyl composition.

EXAMPLE IV

Preparation of 1-alkyl-2-acetoyl-sn-glycero-3-phosphocholine from a 1-alkyl-glycerol Chimyl alcohol (predominately 1-hexadecylglycerol) having the formula

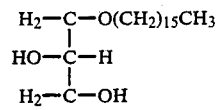

(available from commercial sources) is benzylated according to the procedure of Sowden, et al., J. Am. Chem. Soc. 63 p. 3244 (1941) by refluxing with stoichiometric benzyl chloride in diethyl ether containing powdered sodium for about 70 hours in the absence of moisture. The precipitated NaCl is filtered and washed with diethyl ether. The diethyl ether solutions are evaporated under vacuum leaving the benzyl derivative having the formula

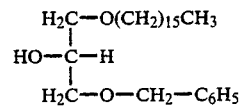

The benzyl derivative is acetylated by reaction with acetic anhydride as described in Example I, step (d), to provide a composition of the formula

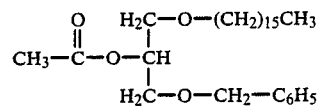

The benzyl group is removed by dissolving the acetylated material in an organic solvent such as n-hexane and hydrogenating the sample in a Parr hydrogenator at 20 psig $H_2$ at room temperature for 5 hours, using palladium black catalyst, to result in the production of 1-hexadecyl-2-acetoyl-sn-glycerol,

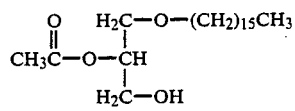

Choline toluene sulfonate is prepared according to the procedure of Brokerhoff et al. Lipids Vol. 14, p. 88, (1978) by neutralizing an aqueous solution of choline hydroxide with p-toluene sulfonic acid. The water is removed by repeated evaporation with toluene, and the product is crystallized as the salt form from acetone and stored in air-tight bottles.

The 1-hexadecyl-2-acetoyl-sn-glycerol is dissolved in ethanol-free chloroform containing an equal molar amount of dry quinoline and an equal molar amount of $POCl_3$. The mixture is heated to about 45° C. for 30 minutes whereupon the 3-OH position is phosphated to produce

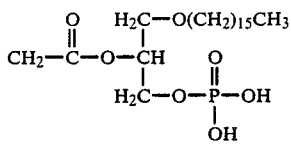

After cooling, twice the stoichiometric amount of choline toluene sulfonate is added, stirring for 5 hours at room temperature. A few milliliters of water is added and stirred for an additional 30 minutes. The mixture is then extracted with several 50 ml portions of chloroform and the extracts are washed successively with water, 3% aqueous Na$_2$CO$_3$, 5% HCl and water. If an emulsion forms, sufficient wash material is added to break the emulsion. The chloroform extract is dried over Na$_2$SO$_4$ and the chloroform is evaporated. The resulting solid material is 1-hexadecyl-2-acetoyl-sn-glycero-3-phosphocholine, which can be purified by thin layer chromatography as described in Example I, section (d).

The foregoing descriptions of the compositions and methods of this invention have been presented for purposes of illustration and description and are not intended to be exhaustive or to limit the invention to the precise forms disclosed. The examples were chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

What is claimed is:

1. A method for treating a warm-blooded animal comprising administering to said animal a composition consisting essentially of a compound having the formula

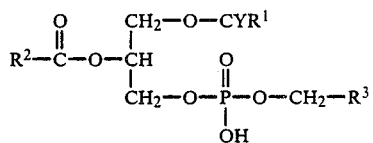

wherein
R$^1$ is an alkyl or alkenyl group having from about 11 to about 23 carbon atoms;
R$^2$ is hydrogen or an alkyl or alkenyl group having from about 1 to about 11 carbon atoms;
R$^3$ is NR$_4$R$_5$ or NR$_4$R$_5$R$_6$=An$^-$
wherein R$_4$, R$_5$ and R$_6$ are independently hydrogen or lower alkyl having from 1 to 3 carbon atoms and An is an anion; and
Y represents the hydrogens of a metheylene group or the oxygen of a carbonyl group
wherein R is a saturated group having from 9 to 21 carbon atoms, or salts or hydrates thereof in an amount sufficient to lower the animal's blood pressure.

2. A method for treating a warm-blooded animal comprising administering to said animal in an amount sufficient to lower the animal's blood pressure a composition comprising a compound having the formula:

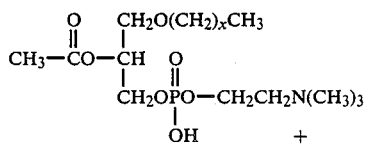

wherein x denotes the integer 15 or 17.

* * * * *